(12) United States Patent
Springer

(10) Patent No.: US 6,288,288 B1
(45) Date of Patent: *Sep. 11, 2001

(54) PROCESS FOR PREPARING SATURATED ALCOHOLS

(75) Inventor: Helmut Springer, Dinslaken (DE)

(73) Assignee: Celanese GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/199,862

(22) Filed: Nov. 25, 1998

(30) Foreign Application Priority Data

Nov. 29, 1997 (DE) .............................. 197 53 157

(51) Int. Cl.$^7$ .................................................. C07C 29/14
(52) U.S. Cl. ............................................................ 568/881
(58) Field of Search ............................................. 568/881

(56) References Cited

U.S. PATENT DOCUMENTS

| | | | | |
|---|---|---|---|---|
| 2,088,015 | * | 7/1937 | Wickert | 588/881 |
| 2,088,016 | * | 7/1937 | Wickert | 568/881 |
| 2,088,017 | | 7/1937 | Wickert et al. | |
| 2,088,018 | * | 7/1937 | Wickert | 568/881 |
| 2,088,019 | * | 7/1937 | Wickert | 568/881 |
| 2,200,216 | * | 5/1940 | Loewenberg | 568/881 |
| 2,852,563 | * | 9/1958 | Hagemeyer | 568/881 |

FOREIGN PATENT DOCUMENTS

| | | | |
|---|---|---|---|
| 141569 | * | 5/1985 | (EP) . |
| 446026 | | 4/1936 | (GB) . |
| 595276 | * | 2/1978 | (SU) . |

OTHER PUBLICATIONS

Astakhova, Maslo–Zhir. Prom–st., (9), pp. 26–27, 1978.*
Voitkevich, Chem. Abstr. 89:42456w, 1978.*
S.G. Powell et a Jour. American Chemical Society, XP–002095352 vol. 66, pp. 372–376, 1944.

* cited by examiner

*Primary Examiner*—Michael L. Shippen
(74) *Attorney, Agent, or Firm*—Bierman, Muserlian and Lucas

(57) ABSTRACT

A process for preparing saturated alcohols comprising effecting an aldol condensation of alkyl methyl ketones of 6 to 8 carbon atoms which are branched at the β-carbon atom with aldehydes of 4 to 15 carbon atoms which are branched at the α-carbon atom to form α,β-unsaturated ketones and subsequent hydrogenation of the α,β-unsaturated ketones to obtain alcohols, wherein the aldol condensation is carried out at a temperature of 60 to 130° C. in the presence of a 30–55% strength aqueous solution of an alkali metal hydroxide resulting in very low by-product formation.

6 Claims, No Drawings

PROCESS FOR PREPARING SATURATED ALCOHOLS

SUMMARY OF THE INVENTION

The present invention relates to a process for preparing saturated alcohols by means of an aldolcondensation of alkyl methyl ketones of 6 to 8 carbon atoms which are branched at the β-carbon atom with aldehydes of 4–15 carbon atoms which are branched at the α-carbon atom to form α,β-unsaturated ketones and subsequent hydrogenation of the α,β-unsaturated ketones to give the corresponding saturated alcohols.

STATE OF THE ART

The aldol addition is the base- or acid-catalyzed addition of activated methylene groups onto the carbonyl groups of aldehydes or ketones with formation of β-hydroxy carbonyl compounds. After a certain reaction time, an equilibrium is established between the β-hydroxy carbonyl compounds and the unreacted starting materials. If the aldol addition is followed by elimination of water, which occurs easily and is the rule when acid catalysts are used, the overall reaction is known as an aldol condensation. Products of the aldol condensation are α,β-unsaturated carbonyl compounds.

In the aldol addition between aldehydes and ketones, the ketones always function as the methylene component as a result of their lower carbonyl activity. The condensation of the keto group with the α-methylene group of an aldehyde is possible only in a few cases via particular intermediates. For this reason, the first products are usually β-hydroxy ketones whose keto group originates from the ketone used. The subsequent elimination of water the β-hydroxy ketones forms the corresponding α,β-unsaturated ketones.

In the reaction between aldehydes and ketones, only a single α,β-unsaturated ketone is obtained as the reaction product if saturated, aliphatic aldehydes without an α-hydrogen atom are used. The self-condensation of the ketone is observed only to a minimal extent. In contrast, when aldehydes having an α-hydrogen atom are used, the self-condensation of the aldehydes has to be expected as an undesired secondary reaction.

While the use of symmetrical ketones always forms only one β-hydroxyketone in the aldol addition, the use of unsymmetrical ketones in which the α-hydrogen atoms are not equivalent makes it possible to form two structurally different β-hydroxyketones according to the reaction scheme I below, where $R_1$ is not hydrogen,

I

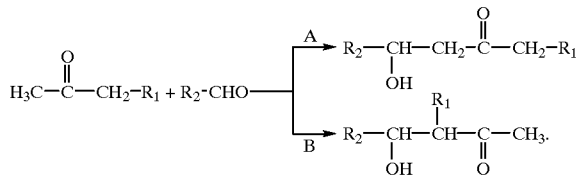

Rules can be formulated for the course of such aldol condensations involving unsymmetrical ketones. Here, a distinction first has to be made between the alkali-catalyzed and the acid-catalyzed aldol condensation. Both the CH-acidity and steric factors determine the course of the reaction.

In the alkali-catalyzed aldol condensation of unbranched aldehydes and α-branched ketones, the abstraction of the proton occurs at the α-carbon atom of the ketone which bears the most substituents (case A). In contrast, when aldehydes which are branched at the α-carbon atom are used, the abstraction of the proton occurs preferentially at the α-carbon atom of the ketone which bears the least substituents (case B). Thus, in case A, the aldol addition forms a β-hydroxyketone in accordance with equation IA, while in case B, the reaction is expected to proceed in accordance with equation IB.

Exceptions to the above rule occur when the ketone is branched in the β position. As a result of the additional steric effect, the condensation here always occurs in accordance with equation IA, regardless of the aldehyde structure. In contrast to alkaline catalysis, the aldol condensation using acid catalysts always, i.e. regardless of the type of branching of the aldehydes and ketones, proceeds in accordance with equation IB.

Undesired secondary reactions of the ketone and aldehyde starting materials which occur concurrently with the aldolization can be, for example, the Cannizzaro reaction and the Claisen-Tishtshenko reaction. Usually, only aromatic and non-aldolizable aliphatic aldehydes, i.e. aldehydes without an α-hydrogen atom, undergo the Cannizzaro reaction and disproportionate in the presence of strong alkalis to form equimolar amounts of alcohol and carboxylic acid. In contrast, in the case of aldolizable aldehydes, the aldol addition and condensation generally occurs exclusively because its rate is higher than that of the Cannizzaro reaction. However, under particular reaction conditions, aldolizable aldehydes having a certain structure with a hydrogen atom in the α position can also undergo the Cannizzaro reaction.

Thus, it is known from U.S. Pat. No. 3,398,166 that C4–16 aldehydes having only one hydrogen atom in the α position disproportionate into the corresponding alcohol and the associated carboxylic acid at 40–250° C. in the presence of a 30–50% strength aqueous solution of an alkali metal hydroxide or alkaline earth metal hydroxide. In the case of 2-ethylhexanal, 48.5% of 2-ethylhexanol and 49% of sodium ethylhexanoate, based on 100% of aldehyde, are formed in the presence of a 50% strength sodium hydroxide solution.

The Claisen-Tishtshenko reaction occurs as a further secondary reaction to the aldol condensation if the catalysts used are aluminum alkoxides which are too weakly basic to catalyze the aldol reaction. In this case, even aldolizable aliphatic aldehydes are converted into the corresponding alkoxide and an ester of the corresponding carboxylic acid in a reaction similar to a Cannizzaro reaction.

Further secondary reactions in the form of subsequent reactions of the reaction products of the aldolization are known. An example of such a reaction is the reaction of the α,β-unsaturated ketone present after the aldol condensation with further aldehyde molecules to form more highly condensed compounds. on this subject, U.S. Pat. No. 3,291,821 reports that $C_{4-10}$-aldehydes having only one hydrogen atom in the a position form glycol monoesters by trimerization even in the presence of an only 5–20% strength aqueous solution of a strong inorganic base at 50–125° C.

Only a small amount of literature exists on the subject of the aldol condensation of ketones which are branched at the β-carbon atom and aldehydes which are branched at the α-carbon atom. British Patent No. 446,026 discloses the aldol condensation of methyl isobutyl ketone with aliphatic aldehydes having at least 8 carbon atoms to form α,β-unsaturated ketones. In particular, the aldol condensation of methyl isobutyl ketone with 2-ethylhexanal at a temperature of less than 25° C. in the presence of a catalyst solution in the form of methanolic potassium hydroxide is described. As an alternative to methanol as solvent for the catalyst, it is also possible to use other substances which are inert toward the reactants but are volatile at the same time, e.g. ethanol. In this case, the described use of alkali metal hydroxides as catalyst has the disadvantage that, as a result of the presence of methanol, a relatively large amount of the alkali metal goes over into the organic product phase formed in the reaction. This product phase has to be appropriately worked up afterwards to remove the alkali metal, e.g. by costly scrubbing with water which in turn leads to large amounts of wastewater contaminated with alkali.

OBJECTS OF THE INVENTION

It is therefore an object of the invention to provide an improved process for preparing saturated alcohols by aldol condensation of ketones which are branched at the β-carbon atom and aldehydes which are branched at the α-carbon atom and subsequent hydrogenation.

This and other objects and advantages of the invention will become obvious from the following detailed description.

THE INVENTION

This object is achieved by a process for preparing saturated alcohols comprising an aldol condensation of alkyl methyl ketones of 6 to 8 carbon atoms which are branched at the β-carbon atom and aldehydes of 4 to 15 carbon atoms which are branched at the α-carbon atom to form α,β-unsaturated ketones and subsequent hydrogenation of the α,β-unsaturated ketones to give the corresponding saturated alcohols, characterized in that the aldol condensation is carried out at a temperature of 60–130° C., preferably 80–120° C., in the presence of a 30–55% strength, preferably 40–50% strength, aqueous solution of an alkali metal hydroxide.

Conversion and selectivity of the process of the invention are excellent. Secondary reactions of the ketone and aldehyde starting materials e.g. in the form of the Cannizzaro or Claisen-Tishtshenko reaction, occur only to a very minimal extent. Thus, for example, the alcohol formed from the aldehyde in the Cannizzaro reaction and the corresponding carboxylic acid is found in the reaction mixture only in minimal amounts of 0.1–0.6%.

This is a surprising result since the reaction conditions selected for the aldol condensation, i.e. the reaction temperature and the high concentration of the aqueous solution of alkali metal hydroxides used as catalyst, should, according to the disclosure of U.S. Pat. Nos. 3,398,166 and 3,291,821, strongly promote these secondary reactions.

In the process of the invention, an equilibrium between the α,β-unsaturated ketones and the unreacted starting compounds is established in the aldol condensation. For example, if use is made of 0.5 mol of a 40% strength aqueous sodium hydroxide solution, based on 1.05 mol of methyl isobutyl ketone and 1.0 mol of 2-ethylhexanal, the equilibrium proportion of the α,β-unsaturated ketone is about 80% after a reaction time of 3 hours.

The reaction time, which is required principally for establishing the equilibrium between the α,β-unsaturated ketones and the unreacted starting compounds, depends on the reaction conditions selected. In particular, it is possible to carry out the process of the invention so that the water formed in the aldol condensation by dehydration of the β-hydroxy carbonyl compound is either continuously separated from the reaction mixture during the reaction or else is not separated off. If the water is removed, for example, by means of a water separator, the reaction time needed to achieve equilibrium when using a 40% strength aqueous solution of the alkali metal hydroxide is about 60 minutes. When the water is not removed, but the conditions are otherwise identical, equilibrium is achieved only after 180–240 minutes, since the concentration of the alkali metal hydroxide solution used gradually decreases because of the water formed.

Thus, for example, the concentration of a 50% strength sodium hydroxide solution of which 0.5 mol is used drops to 34% by the time 1 mol of aldehyde has been quantitatively converted. When using a 40% strength sodium hydroxide solution, a drop in the concentration to 29% is observed under analogous conditions.

Preference is therefore given to the embodiment of the process of the invention with removal of the water of reaction, in which the original concentration of the alkali metal hydroxide solution is thus kept constant over the entire reaction time. This process variant has the additional advantage that the catalyst-containing aqueous phase at the end of the reaction, i.e. when the equilibrium state is reached, can, after separating off the organic product phase, be recycled a plurality of times without further treatment.

The process of the invention is carried out using alkyl methyl ketones which have 6 to 8 carbon atoms which are branched at the β-carbon atom, preferably methyl isobutyl ketone, and aldehydes which have 4 to 15, preferably 5 to 12, carbon atoms and are branched at the α-carbon atom, in particular 2-ethylhexanal.

The ketone which is branched at the β-carbon atom, the aldehyde which is branched at the α-carbon atom and the alkali metal hydroxide present in aqueous solution are used in a molar ratio of (0.90–1.1):1:(0.15–1), preferably (0.95–1):1:(0.35–0.75). Larger excesses of ketone give no selectivity improvements and higher amounts of aldehyde give no advantage in terms of conversion.

The process of the invention can be carried out continuously or batchwise; but preference is given to the continuous mode of operation.

The hydrogenation is usually carried out in the heterogeneous phase over Raney nickel or supported metal catalysts, preferably nickel catalysts, at temperatures of 80–180° C., preferably 100–140° C., and pressures of 1–30 MPa, preferably 8–12 MPa. Hydrogenations under these conditions are generally known and are described, for example, in Methodicum Chimicum, Volume 5, edited by J. Falbe, 1975, pages 47ff.

In particular, the process of the invention is suitable for preparing 7-ethyl-2-methyl-4-undecanol (tetradecanol) by aldol condensation of methyl isobutyl ketone and 2-ethylhexanal at 90–110° C. in the presence of a 40–50% strength aqueous sodium hydroxide solution to form 7-ethyl-2-methylundec-5-en-4-one with subsequent hydrogenation to give the above-mentioned alcohol. The hydrogenation catalyst used here is, preferably, a nickel catalyst supported on kieselguhr.

Depending on the conditions selected for the aldol condensation and the associated content of α,β-unsaturated ketone in the reaction mixture of the aldol condensation, the hydrogenation mixture contains up to 85% of 7-ethyl-2-methyl-4-undecanol.

In the following examples, there are described several preferred embodiments to illustrate the invention. However, it is to be understood that the invention is not intended to be limited to the specific embodiments.

EXAMPLE 1

Preparation of 7-ethyl-2-methyl-4-undecanol

From separate reservoirs, 400.0 g of 50% strength sodium hydroxide solution and a mixture of 1,062.0 g (10.6 mol) of methyl isobutyl ketone and 1,294.0 g (10.1 mol) of 2-ethylhexanal were introduced dropwise into a 4 liter round-bottom flask over a period of 100 minutes while mixing well. The mixture was then heated to 100° C. and stirred for 60 minutes. After the reaction is complete, the mixture is allowed to cool. According to gas-chromatographic analysis, the organic phase (2215.0 g) had the following composition:

| | |
|---|---|
| 8.2% | methyl isobutyl ketone |
| 4.0% | 2-ethylhexanal |
| 0.2% | 2-ethylhexanol |
| 78.9% | 7-ethyl-2-methylundec-5-en-4-one |
| 8.7% | others. |

Based on the 2-ethylhexanal used, the yield of 7-ethyl-2-methylundec-5-en-4-one was 82.3% of theory.

The product can be used directly in the hydrogenation without any further purification operations. The hydrogenation was carried out at a temperature of 120° C. and a pressure of 10 MPa in the presence of a Ni catalyst ™CelActiv Ni 52/35. This Ni catalyst is a commercial product of Celanese GmbH. The hydrogenation product had the following composition:

| | |
|---|---|
| 8.4% | 2-methyl-4-pentanol |
| 4.0% | 2-ethylhexanol |
| 78.3% | 7-ethyl-2-methy-4-undecanol |
| 9.3% | others. |

The 7-ethyl-2-methyl-4-undecanol was obtained in pure form by final distillation at 132° C. and a pressure of 10 mbar.

EXAMPLE 2

Preparation of 7-n-propyl-2-methyl-4-dodecanol

From separate reservoirs, 62.5 g of 40% strength sodium hydroxide solution and a mixture of 265.5 g of methyl isobutyl ketone (2.65 mol) and 390.0 g of 2-n-propylheptanal (2.50 mol) were introduced dropwise into a 1 liter round-bottom flask over a period of 90 minutes while stirring well. The mixture was then subsequently heated to 108–110° C. and stirred for 4 hours. After the reaction was complete, the mixture was allowed to cool. According to gas-chromatographic analysis, the organic phase (621.9 g) had the following composition:

| | |
|---|---|
| 11.0% | methyl isobutyl ketone |
| 13.1% | 2-n-propylheptanal |
| 0.9% | 2-n-propylheptanol |
| 70.1% | 7-n-propyl-2-methyldodec-5-en-4-one |
| 4.9% | others. |

Based on the 2-propylheptanal used, the yield of 7-n-propyl-2-methyldodec-5-en-4-one was 73.3% of theory.

The product was hydrogenated at a temperature of 120° C. and a pressure of 10 MPa in the presence of an Ni catalyst ™CelActiv Ni 52/35. The 7-n-propyl-2-methyl-4-dodecanol was obtained in pure form by final distillation at 170° C. and a pressure of 50 mbar.

EXAMPLE 3

Preparation of 2,7-dimethyl-4-nonanol

From separate reservoirs, 62.5 g of 40% strength sodium hydroxide solution and a mixture of 265.5 g of methyl isobutyl ketone (2.65 mol) and 215.0 g of 2-methylbutanal (2.50 mol) were introduced dropwise into a 1 liter round-bottom flask over a period of 90 minutes while stirring well. The mixture was then heated to 90° C. and stirred for 4 hours. After the reaction was complete, the mixture was allowed to cool. According to gas-chromatographic analysis, the organic phase (438.5 g) had the following composition:

| | |
|---|---|
| 1.0% | 2-methylbutanal |
| 7.6% | methyl isobutyl ketone |
| 0.5% | 2-methylbutanol |
| 73.2% | 2,7-dimethylnon-5-en-4-one |
| 18.2% | others. |

Based on the 2-methylundecanal used, the yield of 2,7-dimethylnon-5-en-4-one was 76.4% of theory.

The product was hydrogenated at a temperature of 120° C. and a pressure of 10 MPa in the presence of an Ni catalyst ™CelActiv Ni 52/35. The 2,7-dimethyl-4-nonanol was obtained in pure form by final distillation at 127° C. and a pressure of 50 mbar.

EXAMPLE 4

Preparation of 2,7-dimethyl-4-hexadecanol

From separate reservoirs, 31.3 g of 40% strength sodium hydroxide solution and a mixture of 132.8 g of methyl isobutyl ketone (1.33 mol) and 230.4 g of 2-methylundecanal (1.25 mol) were introduced dropwise into a 1 liter round-bottom flask over a period of 90 minutes while mixing well. The mixture was then heated to 112–118° C. and stirred for 4 hours. After the reaction was complete, the mixture was allowed to cool. According to gas-chromatographic analysis, the organic phase (621.9 g) had the following composition:

| | |
|---|---|
| 10.8% | methyl isobutyl ketone |
| 8.4% | 2-methylundecanal |
| 0.9% | 2-methylundecanol |
| 77.6% | 2,7-dimethylhexadec-5-en-4-one |
| 3.2% | others. |

Based on the 2-methylundecanal used, the yield of 2,7-dimethylhexadec-5-en-4-one was 78.0% of theory.

The product was hydrogenated at a temperature of 120° C. and a pressure of 10 MPa in the presence of an Ni catalyst ™CelActiv Ni 52/35. The 2,7-dimethyl-4-hexadecanol was obtained in pure form by final distillation at 221° C. and a pressure of 50 mbar.

EXAMPLES 5–17

Batchwise aldol condensation of methyl isobutyl ketone and 2-ethylhexanal to give 7-ethyl-2-methylundec-5-en-4-one (I) without removal of water The aldol condensations of Examples 5–17 were carried out according to the following method:

The mixture of methyl isobutyl ketone and 2-ethylhexanal and also the sodium hydroxide solution were introduced dropwise into a 500 ml round-bottom flask over a period of 10 minutes. The exothermic reaction which occurred immediately caused the temperature to rise to 40–50° C. After the dropwise addition was complete, the desired reaction temperature was reached in 10–25 minutes by additional input of heat. The starting point for determining the reaction time was the time at which the reaction temperature was reached; and the heating phase was thus not included.

The concentration of the aqueous sodium hydroxide solution, the amount of aqueous sodium hydroxide solution, based on the aldehyde, reaction time and temperature are shown in the following tables.

TABLE 1

| Example | 5 | 6 | 7 | 8 |
| --- | --- | --- | --- | --- |
| Reaction time (min.) | 240 | 240 | 240 | 120 |
| Molar ratio of ketone:aldehyde:NaOH (1.05:1: X) X | 0.25 | 0.375 | 0.5 | 0.75 |
| Proportion of I in the crude product | 64.9 | 72.5 | 74.8 | 73.8 | a 50% strength sodium hydroxide solution and a reaction temperature of 80° C. are used.

TABLE 2

| Example | 9 | 10 | 11 |
| --- | --- | --- | --- |
| Reaction time (min.) | 240 | 240 | 240 |
| Concentration of NaOH (%) | 30 | 40 | 50 |
| Proportion of I in the crude product | 68.1 | 78.3 | 79.4 | a molar ratio of ketone: aldehyde: NaOH of 1.05 : 1 : 0.5 and a temperature of 100° C. were employed.

TABLE 3

| Example | 12 | 13 | 14 | 15 | 16 | 17 |
| --- | --- | --- | --- | --- | --- | --- |
| Reaction time (min.) | 240 | 240 | 240 | 120 | 60 | 60 |
| Reaction temperature (° C.) | 60 | 80 | 90 | 100 | 110 | 120 |
| Proportion of I in the crude product | 71.3 | 74.8 | 79.1 | 79.5 | 77.2 | 72.5 |

* a molar ratio of ketone: aldehyde: NaOH of 1.05:1:0.5 and a temperature of 100° C. were employed.

EXAMPLES 18–24

Batchwise aldol condensation of methyl isobutyl ketone and 2-ethylhexanal to give 7-ethyl-2-methylundec-5-en-4-one (I) with removal of the water of reaction The experimental procedure in Examples 18–24 was first similar to that of Examples 5–17. After the dropwise addition of the aqueous sodium hydroxide solution and the mixture of methyl isobutyl ketone and 2-ethylhexanal was complete and the reaction mixture had been heated to the reaction temperature, the pressure in the apparatus was reduced until the mixture started to boil and during the further course of the reaction was set so that the desired reaction temperature was maintained. The amount of water of reaction which was theoretically expected in each case was now selectively distilled off by a water separator so that the alkali concentration used at the beginning remained largely constant over the course of the reaction.

The concentration of the aqueous sodium hydroxide solution, the reaction time and the reaction temperature used in Examples 18–23 are shown in Table 4 below. All examples were carried out using a molar ratio of ketone: aldehyde: NaOH of 1.05:1:0.5.

TABLE 4

Influence of the reaction temperature when using different concentrations of sodium hydroxide.

| Example | 18 | 19 | 20 | 21 | 22 | 23 |
| --- | --- | --- | --- | --- | --- | --- |
| Concentration of the NaOH | 30 | 30 | 40 | 40 | 50 | 50 |
| Reaction Time (min.) | 135 | 135 | 75 | 75 | 135 | 15 |
| Reaction Temperature (° C.) | 90 | 100 | 90 | 100 | 90 | 100 |
| Proportion of I in the crude product | 42.7 | 74.2 | 73.0 | 80.6 | 78.9 | 79.1 |

As can be seen from Table 4, the reaction time necessary for establishment of equilibrium was reduced, compared to the experiments without removal of water from about 3 hour to 1 hour.

Example 24 below demonstrates a further advantage of this embodiment of the process of the invention. The reaction was carried out using a molar ratio of methyl isobutyl ketone: 2-ethylhexanal: NaOH of 1.05:1:0.5 and a 40% strength sodium hydroxide solution at a reaction temperature of 100° C., a pressure of 500 mbar and a reaction time of 60 minutes, with the catalyst phase being reused five times. The proportion of 7-ethyl-2-methylundec-5-en-4-one present in the respective product mixture is shown in Table 5.

It can be seen that as the number of times the catalyst phase was recycled increases, the content of 7-ethyl-2-methylundec-5-en-4-one dropped by only 2.8% from 81.1% to 78.3% (after the 4th reuse) with a slight increase in selectivity.

TABLE 5

| Example 24 | After the 1st aldol condensation | Reuse | | | |
|---|---|---|---|---|---|
| | | 1 | 2 | 3 | 4 |
| Proportion of 7-ethyl-2-methylundec-5-en-4-one | 81.12 | 80.75 | 79.25 | 77.76 | 78.34 |

Various modifications of the process of the invention may be made without departing from the spirit or scope thereof and it should be understood that the invention is intended to be limited only as defined in the appended claims.

What I claim is:

1. A process for preparing saturated alcohols comprising effecting
   1) an aldol condensation of alkyl methyl ketones of 6 to 8 carbon atoms which are branched at the β-carbon atoms with aldehydes of 5 to 15 carbon atoms which are branched at the α-carbon atom to form α,β-unsaturated ketones and
   2) subsequent hydrogenation of the α,β-unsaturated ketones to obtain saturated alcohols, wherein the aldol condensation is carried out at a temperature of 60–130° C., in the presence of 30–55% strength aqueous solution of an alkali metal hydroxide and wherein the ketone which is branched at the β-carbon atom, the aldehyde which is branched at the α-carbon atom and the alkali metal hydroxide present in aqueous solution are used in a molar ratio of (0.90–1.1):1:(0.15–1).

2. The process of claim 1 wherein the water formed in the aldol condensation in step 1 is continually separated off from the reaction mixture during the reaction.

3. The process of claim 1 wherein methyl isobutyl ketone is used.

4. The process of claim 3 wherein the aldehyde which is branched at the α-carbon atom is 2-ethylhexanal.

5. The process of claim 1 wherein the molar ratio is (0.95–1):1:(0.35–0.75).

6. The process of claim 1 wherein the aldol condensation is carried out at a temperature of 80 to 120° C. in the presence of a 40 to 50% strength aqueous solution of an alkali metal hydroxide.

* * * * *